(12) United States Patent
Howse et al.

(10) Patent No.: US 8,399,004 B2
(45) Date of Patent: Mar. 19, 2013

(54) LIPID CARRIERS

(75) Inventors: Philip Howse, Southampton (GB); Karen Underwood, Southampton (GB)

(73) Assignee: Exosect Limited, Southhampton, Hampshire (GB)

( * ) Notice: Subject to any disclaimer, the term of this patent is extended or adjusted under 35 U.S.C. 154(b) by 1401 days.

(21) Appl. No.: 10/537,210

(22) PCT Filed: Dec. 5, 2003

(86) PCT No.: PCT/GB03/05311
§ 371 (c)(1), (2), (4) Date: Jun. 3, 2005

(87) PCT Pub. No.: WO2004/049807
PCT Pub. Date: Jun. 17, 2004

(65) Prior Publication Data
US 2006/0051388 A1    Mar. 9, 2006

(30) Foreign Application Priority Data
Dec. 5, 2002 (GB) .................. 0228421.4

(51) Int. Cl.
*A01N 25/26* (2006.01)
*A01N 25/00* (2006.01)
(52) U.S. Cl. ........ 424/406; 424/409; 424/489; 424/417; 424/405; 424/418
(58) Field of Classification Search .......... None
See application file for complete search history.

(56) References Cited

U.S. PATENT DOCUMENTS

| | | | |
|---|---|---|---|
| 3,767,783 A | 10/1973 | Fischer et al. | |
| 4,289,795 A * | 9/1981 | Bogentoft et al. | 427/2.21 |
| 5,162,014 A | 11/1992 | Moore et al. | |
| 5,771,628 A | 6/1998 | Nobbs | |
| 5,885,486 A * | 3/1999 | Westesen et al. | 428/402.24 |
| 6,015,773 A * | 1/2000 | Wysong et al. | 504/360 |

FOREIGN PATENT DOCUMENTS

| | | |
|---|---|---|
| EP | 0118667 A | 9/1984 |
| WO | WO94/00980 | 1/1994 |
| WO | WO-97/33472 | 9/1997 |
| WO | WO00/01236 | 1/2000 |
| WO | WO 0001236 A1 * | 1/2000 |

OTHER PUBLICATIONS

Salini et al., American J. Roentgenology, 1988, 150(4), 735-743.*
Ferreira et al., J. Magnetisim and Magnetic Materials, 2005, 289, 442-444.*
Prosecution History for Australian Patent Application No. 2003285594.
South Africa Patent Certificate No. 2005/04316 dated Jul. 26, 2006.
Prosecution History for Indian Patent Application No. 2969/DELNP/2005.
Prosecution History for PCT/GB03/05311.
Prosecution History for European Patent Application No. 03778593.8.
Notice of Allowance dated Apr. 17, 2009 for Chinese Patent Application No. 200380105234.2.
Response to Telephone Discussion for Chinese Patent Application No. 200380105234.2 filed Mar. 2, 2009.
Request for Examination for Chinese Patent Application No. 200380105234.2 filed Jun. 19, 2008.
Rejection Decision dated Mar. 7, 2008 for Chinese Patent Application No. 200380105234.2.
Response to Second Office Action for Chinese Patent Application No. 200380105234.2 filed Aug. 21, 2007.
Notification of Second Office Action dated Apr. 6, 2007 for Chinese Patent Application No. 200380105234.2.
Response to First Office Action for Chinese Patent Application No. 200380105234.2 filed Jan. 18, 2007.
Notification of First Office Action dated Jul. 7, 2006 for Chinese Patent Application No. 200380105234.2.

* cited by examiner

*Primary Examiner* — Daniel Sullivan
*Assistant Examiner* — Kyle Purdy
(74) *Attorney, Agent, or Firm* — Patterson & Sheridan, LLP (57) ABSTRACT

There is disclosed a method of controlling pests which comprises exposing a surface of the pest to a particulate composition containing particles of an initially unmagnetized material, which is capable of becoming magnetically polarized when subjected to an electric or magnetic field, the said particles being associated with at least one pesticide or behavior modifying chemical.

19 Claims, 6 Drawing Sheets

Mean Percentage Cumulative Mortality of
*Blatella germanica* (n=3)

LIPID CARRIERS

The present invention relates to a method of controlling insects and other arthropod pests, such as ticks and mites, by contaminating the pests with fine coated metallic particles formulated with biologically active compounds, such that the contamination is disseminated to other individuals in the population by contact. This process, known as autodissemination, is analogous to the spread of disease-causing microorganisms in man by contact.

The method is particularly suitable for flying or crawling insects, mites and ticks, including pests encountered in agriculture, horticulture, forestry and public health. Such pests include (among others) ants and termites, lepidopteran pests (moths), flies (e.g. fruit flies, tsetse flies, biting flies, houseflies and mosquitoes), cockroaches and coleopteran pests (e.g. beetle pests of forestry plantations).

The widespread use of chemical pesticides in crop protection has led to the development of resistance to a wide range of pesticides in many species of insect, and the resistance continues to develop. In attempts to counter resistance, overuse of pesticides and the resulting environmental and crop pollution and mortality of beneficial insects have also resulted in more and more insecticides in common use being withdrawn from registration throughout the world, particularly in the European community and North America. Both of these factors make it desirable to develop new control measures that present fewer hazards to farmers, consumers and the environment, targeting the pest species effectively and minimising the amounts of pesticidal substances used.

WO 94/00980 describes a method of controlling pests, such as insects, involving the use of electrostatically charged powders, in which the powders are used to adhere to the insect cuticle and also act as carriers for pesticides or other biologically active compounds.

The main disadvantage of electrostatically charged particles is that they must first be charged before they can be applied to the pests, such as for example by friction. Another disadvantage is that the particles can be dislodged or removed from baited surfaces by wind or by shaking. The electrostatic charge of the particles may also be undermined in conditions of high humidity and when moisture films develop.

WO 00/01236 describes a method of controlling pests, such as insects, by trapping and/or killing them wherein the pest is exposed to a composition comprising particles containing or consisting of at least one magnetic material. The said application also describes particles which have an inert core which acts as a carrier for biologically active materials, the core being coated with a permanently magnetic material.

The use of magnetic materials of the form as described in WO 00/01236 has the following disadvantages. First, the magnetic surface has very poor retention properties for active ingredients, especially if, as is commonly the case, the active ingredients are very volatile. Secondly, active ingredients contained within the inner core of a magnetically-coated particle are not easily accessible to the surface of the pest. Thirdly, the magnetic particles are "hard" magnets which retain their magnetism, as opposed to "soft" magnets of the type used, for example, in solenoids, in which the magnetism is lost immediately that they are removed from a magnetic or electric field. Hard magnetic particles are difficult to produce in a specified size range, weight or shape because they lose their magnetism, when milled. Fourthly, because the only economic source of hard magnetic particles is from the finings of mining operations, toxic metallic salts may be present as contaminants, and it would be undesirable to introduce these into a crop environment.

We have now developed a method and apparatus for controlling pests which involves the use of metallic particles which are initially unmagnetised but which are capable of becoming magnetically polarised when subjected to an electric field in close proximity thereto such as that provided by the insect body. Such particles will be unaffected by moisture or humidity and, when anchored on a conducting or magnetic surface will remain in position for long periods of time. This invention therefore differs from that described in WO 00/01236 which specifically excludes the possibility of the use of metallic particles or non-magnetically polarised materials such as ferrous iron, unless they are admixed with hard magnetic materials and therefore pre-magnetised.

Accordingly, the present invention provides a method of controlling pests which comprises exposing a surface of the pest to a particulate composition containing particles of an initially unmagnetized material, which is capable of becoming magnetically polarized when subjected to an electric or magnetic field, the said particles being associated with at least one pesticide or behaviour modifying chemical.

By the term "pesticide" as used herein is meant an insecticide, acaricide, fungicide, insect growth regulator, chemosterilant, bacterium, fungus or virus.

In another aspect the present invention provides a pesticidal composition in particulate form which comprises particles of an initially unmagnetized material, which is capable of becoming magnetically polarized on exposure to an electric or magnetic field, the said particles being associated with at least one pesticide or behaviour modifying chemical.

The particles may be milled down to a preferred size range, weight or shape, such that they may, if desired, detach easily from the surface of the insect on contact. Furthermore, the particles may be prepared from metallic iron, for example, which is free from possible contaminants.

A preferred aspect of the present invention is the use of metallic particles coated with a material which acts as a carrier for a pesticide or a behaviour modifying compound such as a pheromone or a compound with a similar action (semiochemicals). Suitable carrier materials are lipids, including fatty acids and their esters, such as stearic acid, stearates, palmitic acid, palmitates etc. which form a coating on the particles and permit the incorporation of any active ingredient which has some lipid solubility therein. In this way, active ingredients are placed in direct contact with the surface of the insect when a coated particle is resting on the insect cuticle.

The efficacy and power of adhesion of electrostatically charged particles depends on their ability to attach to the insect cuticle because it is an electret, i.e. it is permanently electrically polarised. The efficacy of certain metallic particles to attach to the cuticle is believed to be due to their property of interaction with the weak electric field generated by the movement of ions within the body of the insect. In the present invention, the metal particles become magnetically polarised in the presence of the electric field at the surface of the living insect and this serves to hold the metal particles against the insect cuticle. It is important to note that the particles acquire their adhesive properties only when they are in contact with the outer surface of the insect and when they are thus acting as miniature solenoids. This is a mode of action distinct from that described in WO 00/01236, in which the particles are premagnetised.

Pesticides in the lipid coating of the attached particles are then able to diffuse into the lipid layers of the insect cuticle and enter the body of the insect. Particles formulated with volatile semiochemicals remain on the surface of the insect acting as emitting sources and biopathogens are anchored onto the body of the insect for long periods thereby facilitating their invasion of the body tissues.

A further preferred aspect of the present invention is the use of powders of a selected size and mass, such that the mass is low enough when the particle is at rest not to overcome the magnetic attraction to the surface of the insect, but high enough to become detached and transferred on contact with the cuticle of a second insect. In this way the optimum amount of transfer of particles will occur between insects, and few particles will fall off when the insect is walking, or in flight.

The biologically active compounds used to effect control of insects include conventional chemical insecticides, biological insecticides, naturally-occurring insecticides and behaviour-modifying compounds, including attractants.

Chemical insecticides are preferably slow-acting, so that the insects survive exposure to the material long enough to pass on the particles to one or more other insects. Naturally-occurring insecticides include materials such as plant extracts and essential oils, including oil of thyme, oil of rosemary, cedarwood oil, neem extract, camphor oil, camomile oil, etc. Biological insecticides are understood to include entomopathogens such as viruses, bacteria (i.e. *Bacillus thuringiensis*), and fungal spores (e.g. *Metarhizium* and *Beauvaria* species). Behaviour modifying compounds are also known as semiochemicals.

A semiochemical is a chemical that affects the behaviour of an organism. Semiochemicals used in communication between members of the same species are known as pheromones, and those involved in communication between members of different species are classed as allelochemicals. Allelochemicals may be involved, for example in, communication between different species of animals, or between plants and animals. Semiochemicals may be attractive or repellent, or have other effects on behaviour. Insect pheromones may be, for example species-specific sex pheromones which can be used to interfere with mate-seeking, aggregation pheromones and alarm pheromones, which can be used to attract insects to baits.

Where a chemical or naturally occurring insecticide or acaricide is used, the amount of active ingredient formulated in the particles will range from 0.001 to 20% by weight. Where an entomopathogen is used, the quantity may be greater, because of the size of the pathogenic organism involved, reaching up to 40% by weight. Where a semiochemical is used, the amount of material required to affect the behaviour of the organism when the particulate material is resting on the body surface may be extremely low in view of the extremely high sensitivity of insect chemical sense organs to certain semiochemicals. A semiochemical present in amounts from 0.1 picograms per particle to 1 microgram per particle will affect behaviour, where the overall particle averages 0.1 to 50 micrometers.

The preferred coating on the metallic particles is lipid in nature, of a material which does not confer strong electrostatic properties, and in which the active ingredients can be absorbed or to which they can be adsorbed. For these reasons coatings of lipid, including fatty acids, their salts and esters, are highly suitable. Other materials which may be used include resins, and polymers with weak tribocharging properties, such as acrylic polymers. The thickness of the coating must satisfy the requirement of permitting the metallic core to come as close as possible to the insect cuticle and that of being of sufficient thickness to sequester the required quantities of the active ingredient. In general, the thickness of the coating will be between 100 nanometers and five micrometers. The physico-chemical nature of the active ingredient may also make the use of a coating unnecessary, for example an oily material can be applied directly to the metallic particles.

Preferably, the metallic material consists of soft iron. In its natural state this is not magnetic and becomes magnetically polarised only when placed in a magnetic or electric field. In the present invention, the particles are unmagnetised and when they are transferred to the insect cuticle by contact they are subject to the weak electric field across the cuticle and so become weakly polarised. Soft iron is one of the group of substances capable of being magnetised, which also includes nickel and cobalt. Metallic nickel and cobalt particles may also be used in the present invention but these are an order of magnitude less susceptible to an electromagnetic field and so are not preferred.

The mass of iron is very high and therefore particles of large size will not stay on the pest. The particles must therefore have a low unit weight, corresponding to that of a sphere of diameter between 0.1 and 50 micrometers. However, a spherical form is not essential, and fine flakes of an equivalent volume are preferred because they will give a greater area of contact with the cuticular surface and are more likely to lodge in folds in the flexible intersegmental membranes of arthropods.

The mode of application of the method of the invention differs according to the type of pest, but in all cases relies on part of the body of the pest coming into contact with powdered material on a coated surface.

The present invention also includes within its scope an insect trap or dispenser in which at least one surface thereof is coated with a pesticide composition of the invention.

In order to control household insect pests such as cockroaches, ants and termites it is desirable to attract the insects into a dispenser, similar to a bait station, into which the insects can easily enter and leave, and in which they are exposed to surfaces coated with the metallic powder. For flying insects, such as moths, beetles, bugs, and flies of various kinds, the powder may be placed in a container into which the insects can easily enter and leave, but come into contact with a layer or coating of lipid-coated particles when they are inside the container.

The present invention will be further described with reference to the accompanying drawings, in which:—

FIG. 1A is a perspective view of an apparatus for the control of crawling insects;

FIG. 1B is a plan view of the apparatus of FIG. 1A with the top surface of the container notionally removed;

FIG. 2 is a perspective view of an apparatus for the control of flying pests;

FIG. 3 is a perspective view of a further apparatus for the control of flying pests;

FIG. 4 is an illustration of the results obtained from an experiment to evaluate the cumulative mortality rate of German cockroaches (*Blattella germanica*) using a biomagnetic composition according to the invention in apparatus as described in FIGS. 1A and 1B compared with 2% chlorpyrifos in a Baygon bait station;

FIG. 5 is an illustration of the results obtained from an experiment to evaluate the powder coverage of the thorax of *Blattella germanica* at various intervals after treatment using the compositions of the invention and other pesticides; and FIG. 6 is an illustration of the results obtained from an experiment to evaluate the secondary transmission of the composition of the invention on a treated insect to an untreated insect.

Referring to FIGS. 1A and 1B, a shallow container 1 is closed at its top and attached to a base plate 2. The container has four separate openings, 3 each of which function as an entrance and an exit for crawling insects, such as ants or cockroaches. The entrances lead through passageways 4 inside the container to a central area 5 which is coated with a powder which comprises soft iron particles coated with a lipid material which is impregnated with a slow-acting insecticide. The soft iron particles are held in place by incorporating a material with conducting or magnetic properties in the central area 5 to which the soft iron particles become attached. The insects, such as cockroaches, are attracted into the container by a chemical or food-based attractant, and in the process of exploration pick up the soft iron particles on their feet and bodies. Individual cockroaches then return to their harbourages and spread the powder to other cockroaches in the harbourage through the mutual contact. The slow-acting insecticide in the lipid layer of the particles is thus spread throughout the colony of cockroaches.

Figure 2:
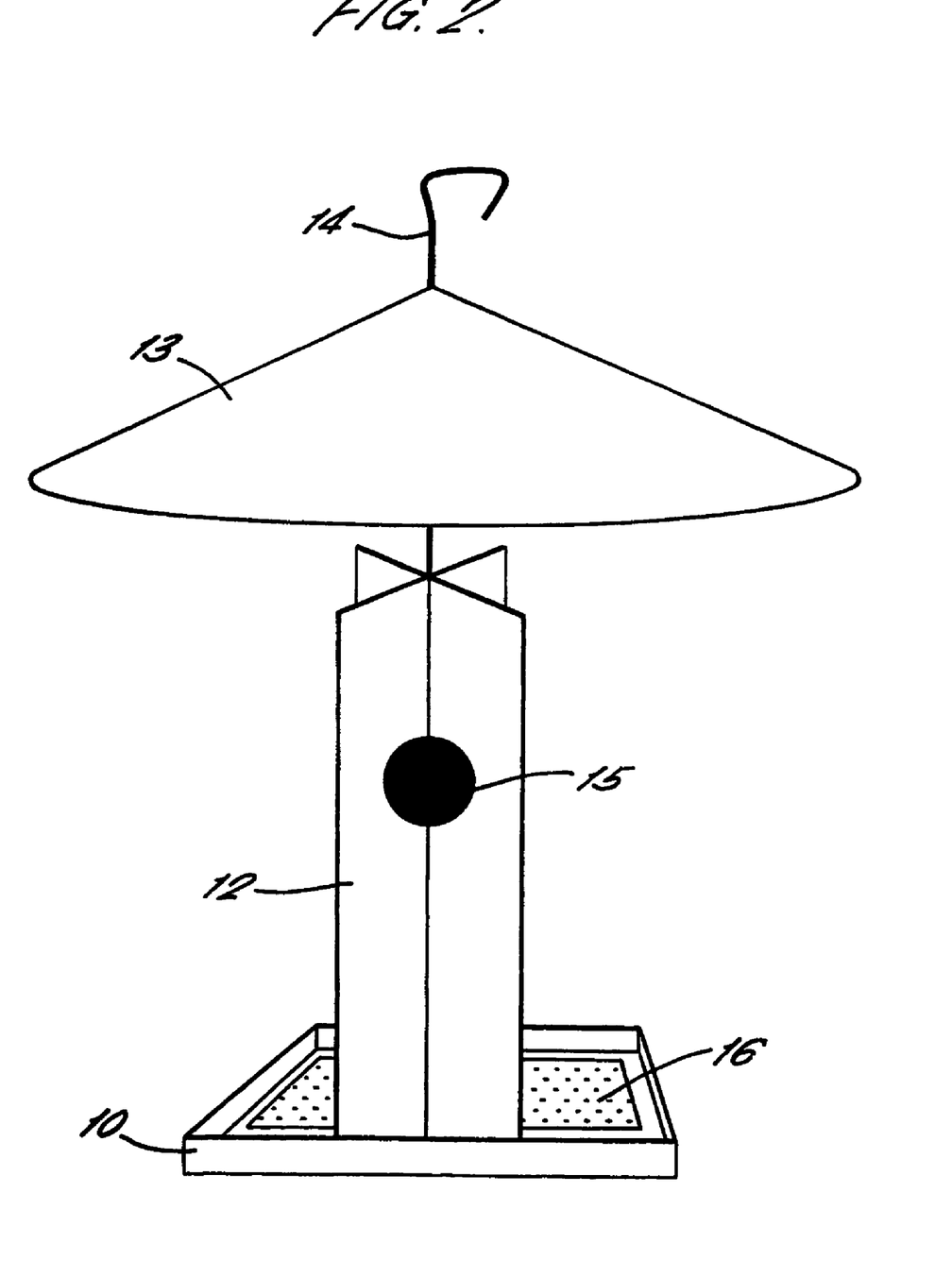

A second aspect of the invention is illustrated in FIG. 2. To control a flying insect pest such as a moth or fruit fly, dispensers are placed in the crop where the moth or fruit fly is a pest. The dispenser consists of a shallow tray 10, to which are attached cross vanes 12. A lid 13 is placed over the cross vanes 12 in order to divert rainwater and debris from landing on the tray. The dispenser is suspended from a branch or other suitable support by the hanger 14. A source 15 of the sexual attractive pheromone of the species is attached to the cross vanes 12 and the vanes 12 are coated with a soft material with a very low coefficient of friction. The tray 10 contains a layer 16 of several grams of coated iron particles formulated with the sexual pheromone of the species.

The flying insects attracted by the pheromone source attempt to alight on the cross vanes 12 but are unable to do so because of the slippery surface thereof. They fall into the tray 10, thereby receiving an inoculum of the powder before flying off. The presence of the pheromone emitting sources on the body of the insect interferes with its ability to detect females of the same species by locating the aerial pheromone trail they produce, and mating does not occur. The mechanisms of interference may include overstimulation or imbalance of stimulation to the sensory receptors, and confusion effects on both male and females produced by males, emitting female signals.

Alternatively, the soft iron particles 16 contained in the tray 10 may be formulated with a slow acting insecticide. Males of the flying insect pest species attracted by the pheromone source alight on the tray 10 and pick up the soft iron particles 16 formulated with the insecticide on their bodies before flying off. During mating quantities of the powder will be spread to other insects of the same species and the slow acting insecticide formulated with the soft iron particles will be spread throughout the local species.

Figure 3:
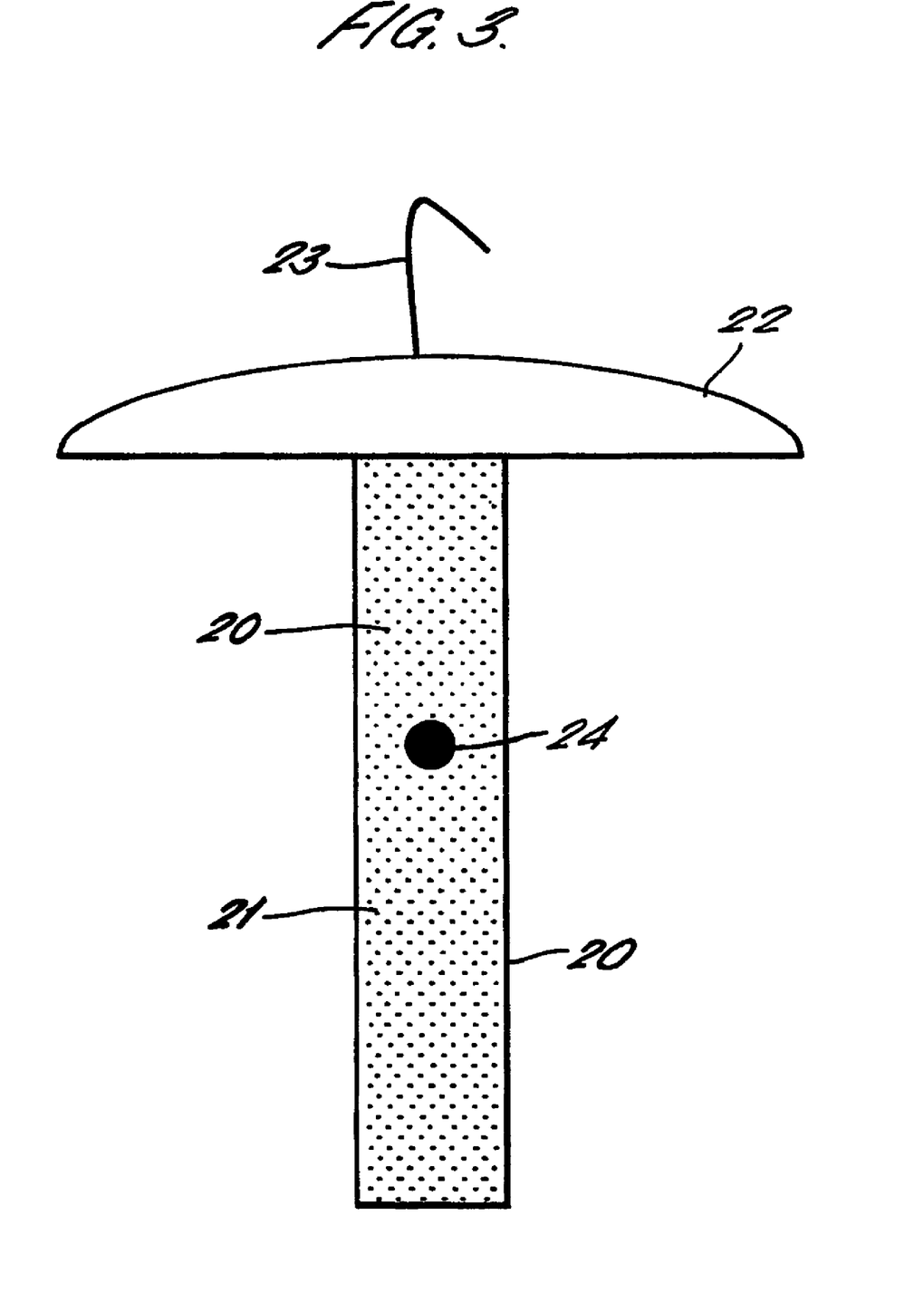
Figure 4:
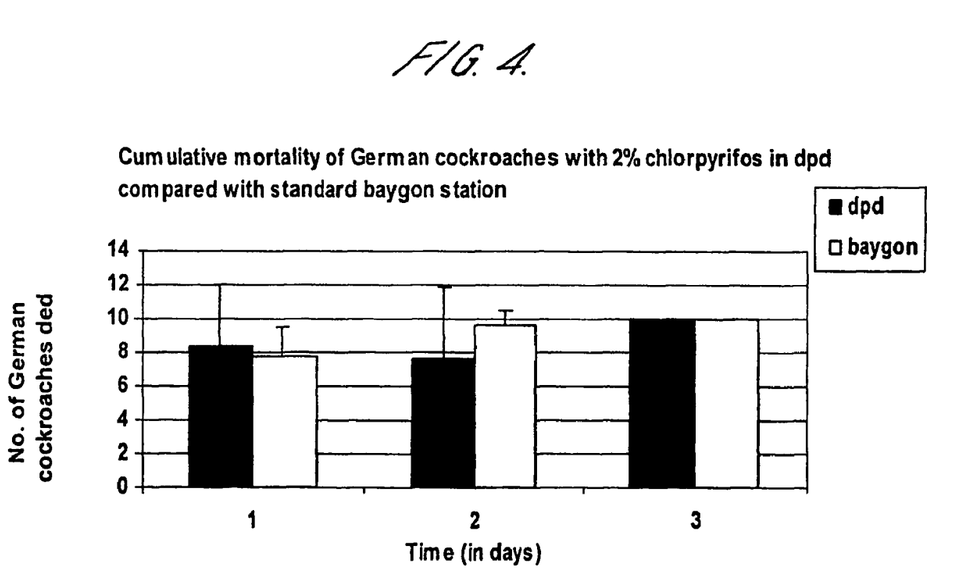

A third aspect of the invention is illustrated in FIG. 3. Again, to control a flying insect pest such as a moth or fruit fly, dispensers are placed in the crop where the moth or fruit fly is a pest. The dispenser consists of a strip of material 20 with conducting or magnetic properties and which is coated with soft iron particles 21. The soft iron particles are anchored by virtue of the conducting or magnetic properties of the strip 20. A lid 22 is placed or suspended over the strip in order to divert rainwater and debris. The dispenser is suspended from a branch or other suitable support by the hanger 23. A source of the sexual attractive pheromone of the species is attached to the strip 24. The soft iron particles anchored to the strip 21 are formulated with the sexual pheromone of the species.

Males of the species attracted by the pheromone source alight on the strip 20 and pick up the powder formulated with pheromone 21 on their bodies before flying off. The presence of pheromone emitting sources on the body of the insect interferes with its ability to detect females by locating the aerial pheromone trail they produce, and mating does not occur.

Alternatively, the soft iron particles 21 anchored to the strip 20 may be formulated with a slow acting insecticide. Males of the flying insect pest species attracted by the pheromone source alight on the strip 20 and pick up the soft iron particles formulated with the slow acting insecticide 21 on their bodies before flying off. During mating, quantities of the powder will be spread to other insects of the same species and the slow acting insecticide formulated with the soft iron particles will be spread throughout the local species.

It will be understood by those skilled in the art that the devices described with reference to FIG. 1A, 1B, 2 or 3 may be modified in their design to take account of differences in the behaviour among the pests that it is desired to control. Furthermore, the means of attracting pests into such devices are not limited to chemical attractants or pheromones. They may include food sources, light, colour, visual patterns, infrared sources, and acoustic sources or a combination of sensory signals, depending upon the attractive power of the signal to the pest concerned.

Figure 1A:
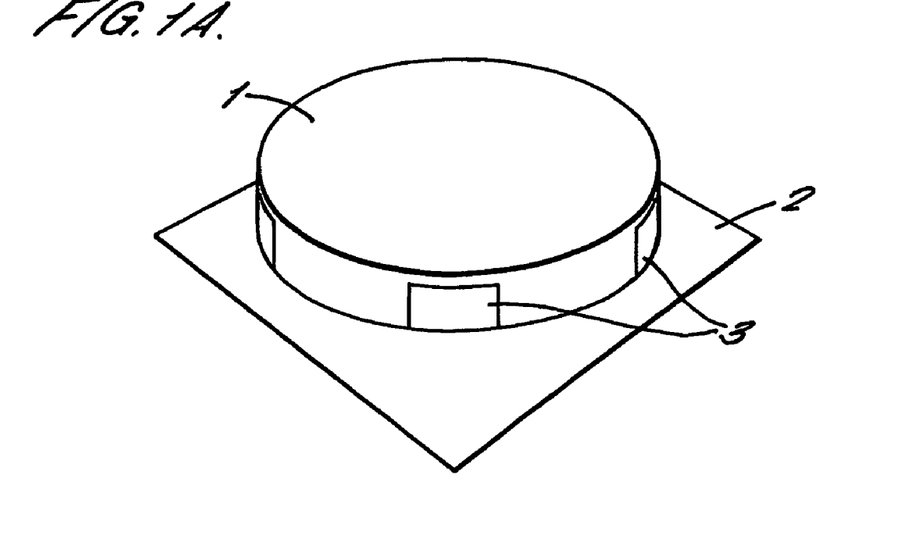
Figure 1B:
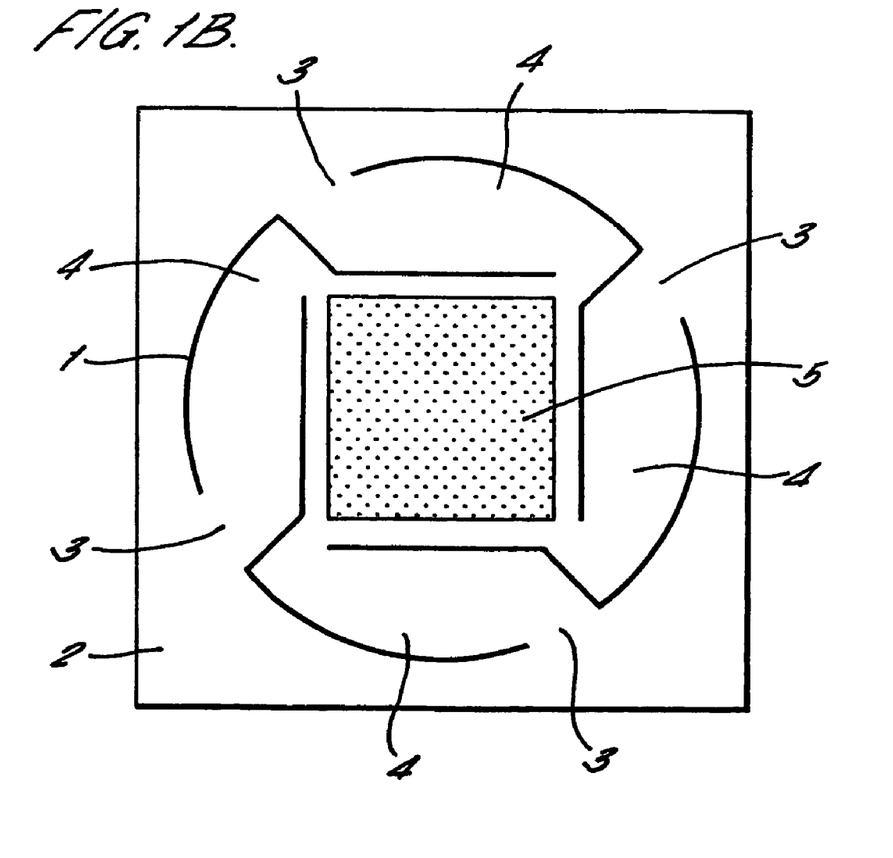

EXAMPLE a) In an experiment to establish the cumulative mortality rate for German cockroaches using a biomagnetic powder, comprising iron flakes of between 5 and 20 microns, ten replicate metal arenas (50 cm×50 cm×30 cm) each containing 10 adult German cockroaches (*Blattella germanica* (L.)) were assembled for both the control and the test item. 0.5 g Chlorpyrifos+biomagnatic powder preparation (0.01 g ai) was placed onto the magnetic material in the centre of a DPD. (Reference to the term DPD means a discrete placement device as shown in FIGS. 1A and 1B). The DPD was baited with an AgriSense lure tablet placed inside the unit. For each of the five treatment replicates a DPD was placed in the left hand lower corner of the arena. For the five standard reference replicates, a Baygon bait station which incorporates 0.125 g Chlorpyrifos was placed in the left hand lower arena. The condition of the cockroaches was assessed at 24 hours intervals.

Figure 5:
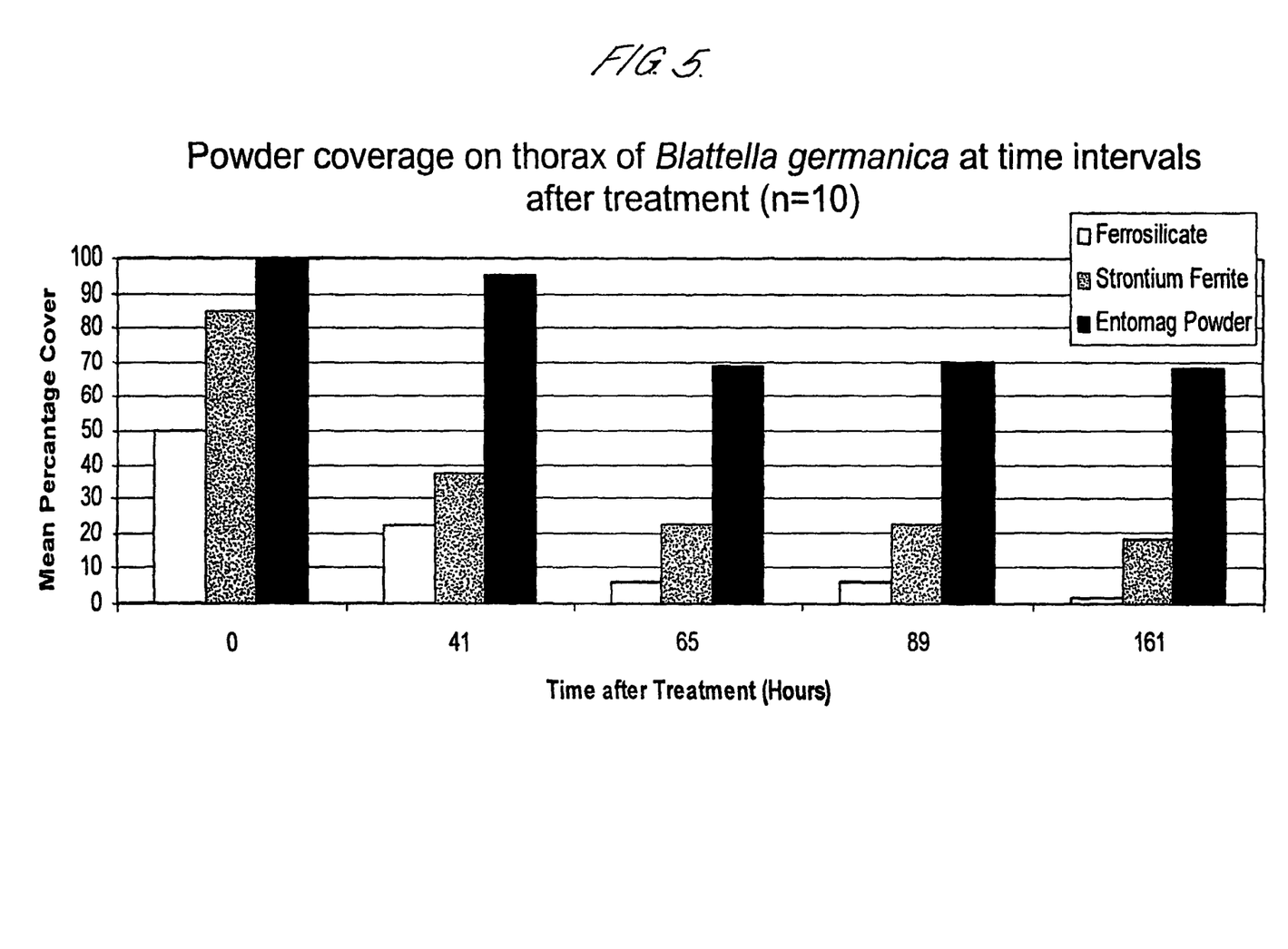
Figure 6:
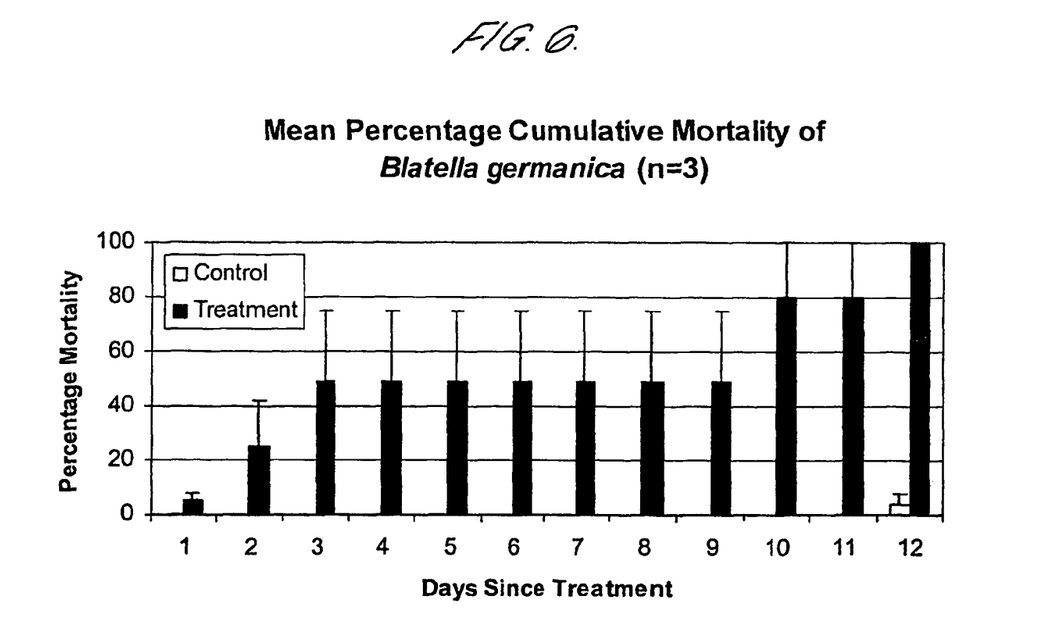

The results of this experiment illustrate the comparison of the biomagnetic composition using the device as hereinbefore described, with reference to FIGS. 1A and 1B and a Baygon bait station, incorporating Chlorpyrifos. Comparable results were obtained despite the fact that only 0.01 of the composition of the present invention was used compared to the 0.125 g chlorpyrifos used in the Baygon station.

b) In an experiment to establish the powder coverage of the thorax of *Blattella germanica* at various time intervals after treatment, 50 *Blattella germanica* adults were placed in a 10 ml container with 5 ml powder to be tested. The container was then agitated gently for 30 seconds. Adults were removed and set up in groups of 10 in culture cages. 10 individuals were sampled at each specified time period and screened for the amount of powder on cuticle. The results in FIG. 5 compare the biomagnetic composition of the present invention to ferrosilicates and strontium ferrite in terms of retention of the powders on the insect. They illustrate the superiority of the composition of the invention that is initially unmagnetised over those pre-magnetised particles.

c) An experiment was carried out to establish the secondary transmission of powder (untreated and treated with pesticides or other behaviour modifying chemical) from a treated insect to an untreated insect. Six replicate arenas (glass, 100×100×30 cm) each containing 24 adult German Cockroaches (*Blattella germanica* (L.)) were assembled for both the control and the test item. Each arena contained a food source (dog biscuits), water source and a cardboard retreat for the cockroaches to aggregate. A 2.5% w/w Chlorpyrifos/biomagnetic powder preparation was applied to an adult cockroach which was then introduced to each treatment in the arena. For the three control replicates, a single cockroach coated in unformulated biomagnetic powder was used. The condition of the cockroaches was assessed at 24 hour intervals. The results illustrate that the powder does pass from treated to untreated insects and ensuring a high mortality rate among insects which are not treated or which have not come into contact with the original dispensing device.

The invention claimed is:

1. A method of controlling pests, comprising:
   exposing a surface of a pest to a particulate composition containing particles of an initially unmagnetized material, which is capable of becoming magnetically polarized when subjected to an electric or magnetic field, said particles being associated with at least one pesticide or behavior modifying chemical, wherein said particles acquire their adhesive properties only when said particles are in contact with an outer surface of the pest, wherein said particles are coated with a material which is a carrier for the pesticide or behavior modifying chemical.

2. A method so claimed in claim 1, wherein said particles comprise a material selected from metallic iron, nickel, cobalt, and mixtures thereof.

3. A method so claimed in claim 1, wherein the carrier comprises a substance selected from a lipid, a resin and a polymer.

4. A method of controlling pests, comprising:
   exposing a surface of a pest to a particulate composition containing particles of an initially unmagnetized material, which is capable of becoming magnetically polarized when subjected to an electric or magnetic field, said particles being associated with at least one pesticide or behavior modifying chemical, wherein said particles acquire their adhesive properties only when said particles are in contact with an outer surface of the pest, wherein said particles are coated with a material which is a carrier for the pesticide or behavior modifying chemical, wherein the carrier comprises a lipid which is a fatty acid, or an ester or salt thereof.

5. A method as claimed in claim 1, wherein said particles have a unit weight corresponding to that of a sphere of a diameter in the range of from 0.1 to 50 micrometers.

6. A method as claimed in claim 1, wherein said particles are associated with the pesticide which is an insecticide, acaricide, fungicide, insect growth regulator or chemosterilant.

7. A method as claimed in claim 1, wherein said particles are associated with the pesticide which is a bacterium, fungus or virus.

8. A method as claimed in claim 1, wherein said particles are associated with the behavior modifying chemical which is a pheromone or allelochemical.

9. A method as claimed in claim 1, wherein said particles are associated with the pesticide that is a chemical or naturally occurring insecticide or acaricide which comprises up to 10% by weight of the particulate composition.

10. A method as claimed in claim 1, wherein said particles are associated with the pesticide that is a bacterium, fungus or virus which comprises up to 40% by weight of the particulate composition.

11. A method as claimed in claim 1, wherein the behavior modifying chemical comprises from 1 picogram to 1 microgram per particle having an average particle size of from 0.1 to 50 micrometers.

12. A method as claimed in claim 1, wherein the pest is lured to a dispenser in which one or more surfaces is coated with the particulate composition.

13. A method as claimed in claim 12, wherein the pest is lured to the dispenser by a chemical attractant, biological attractant, food source, light, color, visual pattern, infra red or acoustic source, or a combination thereof.

14. A method as claimed in claim 1, wherein said particles are coated directly with the pesticide or behavior modifying chemical.

15. A method as claimed in claim 2, wherein said particles are coated directly with the pesticide or behavior modifying chemical.

16. A method as claimed in claim 2, further comprising luring the pest to a dispenser in which one or more surfaces is coated with the particulate composition.

17. A method as claimed in claim 3, wherein said particles are associated with the pesticide which is selected from an insecticide, an acaricide, a fungicide, an insect growth regulator and a chemosterilant.

18. A method as claimed in claim 3, wherein said particles are associated with the behavior modifying chemical which is selected from a pheromone and an allelochemical.

19. A method of controlling pests, comprising:
    exposing a surface of a pest to a particulate composition containing particles of an initially unmagnetized material, which is capable of becoming magnetically polarized when subjected to an electric or magnetic field, said particles being associated with at least one pesticide or behavior modifying chemical, wherein said particles acquire their adhesive properties only when said particles are in contact with an outer surface of the pest, wherein said particles are coated with a material which is a carrier for the pesticide or behavior modifying chemical, wherein the thickness of the coating is between 100 nanometers and five micrometers.

* * * * *

UNITED STATES PATENT AND TRADEMARK OFFICE
CERTIFICATE OF CORRECTION

PATENT NO. : 8,399,004 B2
APPLICATION NO. : 10/537210
DATED : March 19, 2013
INVENTOR(S) : Howse et al.

It is certified that error appears in the above-identified patent and that said Letters Patent is hereby corrected as shown below:

In the Specification:

Column 1, Lines 64-65, please delete "finings" and insert -- fines -- therefor.

Signed and Sealed this
Eleventh Day of June, 2013

Teresa Stanek Rea
*Acting Director of the United States Patent and Trademark Office*